(12) United States Patent
Chen et al.

(10) Patent No.: US 11,744,894 B2
(45) Date of Patent: Sep. 5, 2023

(54) COMPOSITE BIOLOGICAL AGENT BASED ON POROUS FRAME MATERIALS

(71) Applicant: NANKAI UNIVERSITY, Tianjin (CN)

(72) Inventors: Yao Chen, Tianjin (CN); Zhenjie Zhang, Tianjin (CN); Yifan Feng, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 95 days.

(21) Appl. No.: 16/960,054

(22) PCT Filed: Jan. 15, 2019

(86) PCT No.: PCT/CN2019/071697
§ 371 (c)(1),
(2) Date: Jul. 3, 2020

(87) PCT Pub. No.: WO2019/141152
PCT Pub. Date: Jul. 25, 2019

(65) Prior Publication Data
US 2020/0397902 A1  Dec. 24, 2020

(30) Foreign Application Priority Data

Jan. 17, 2018 (CN) .......................... 201810044187.3
Jan. 4, 2019 (CN) .......................... 201910008528.6

(51) Int. Cl.
*A61K 47/24* (2006.01)
*A61K 35/761* (2015.01)
*A61K 39/395* (2006.01)
*A61K 47/02* (2006.01)

(52) U.S. Cl.
CPC ............ *A61K 47/24* (2013.01); *A61K 35/761* (2013.01); *A61K 39/3955* (2013.01); *A61K 47/02* (2013.01)

(58) Field of Classification Search
CPC .. A61K 47/24; A61K 35/761; A61K 39/3955; A61K 47/02
See application file for complete search history.

(56) References Cited

FOREIGN PATENT DOCUMENTS

| CN | 104087572 | * | 10/2014 | ............. C12N 11/14 |
| CN | 104087572 A | | 10/2014 | |
| CN | 106715690 | * | 5/2017 | |
| WO | WO-2016207397 A1 | * | 12/2016 | ............. A61K 31/19 |
| WO | WO-2018000043 A1 | * | 1/2018 | |

OTHER PUBLICATIONS

CN104087572 Machine Translation (Year: 2014).*
CN106715690 Machine Translation (Year: 2017).*
Sun, et al., Pore Environment Control and Enhanced Performance Enzymes Infiltrate in Covalent Organic Frameworks, Journal of the American Chemical Society, Dec. 25, 2017, 984-992, vol. 2018, 140, American Chemical Society, U.S.A.
Liang, et al., Biomimetic Mineralization of Metal-organic Frameworks as Protective Coatings for Biomacromolecules, Nature Communications, Jun. 4, 2015, vol. 6, 7240, Macmillan Publisher Limited, U.S.A.

* cited by examiner

*Primary Examiner* — Sean M Basquill

(57) ABSTRACT

A novel composite biological agent based on a porous frame material, comprising porous frame materials and biomolecules. The porous frame materials cover a biological product, wherein the porous frame materials are metal-organic frame material (MOFs), covalent organic frame materials (COFs), and hydrogen-bonding organic frame materials (HOFs), and the biomolecules are any one or a combination of antibodies, enzymes, peptides, vaccines, nucleotides, and virus species. The composite biological agent uses the porous frame materials and biomolecules to form a porous frame material/biomolecule complex, and the biomolecules are coated to achieve the protection effect. Under the premise of remaining biomolecule activity, the system can achieve efficient separation and recovery of the porous materials and the biomolecules, so that the technical problems of synthesis, storage, release, etc. are solved, a good technical effect is achieved, and the biomolecules are effectively protected. The system is applied to the storage and transportation of biological agents and preparation of novel agents.

1 Claim, 13 Drawing Sheets

COMPOSITE BIOLOGICAL AGENT BASED ON POROUS FRAME MATERIALS

RELATED APPLICATIONS

The present application is a national phase application of the International Application PCT/CN2019/071697 filed Jan. 15, 2019, which claims the benefit of the Chinese Patent Applications CN201810044187.3 filed Jan. 17, 2018 and CN201910008528.6 filed Jan. 4, 2019, each of which is incorporated herein by reference in its entirety.

FIELD OF THE INVENTION

The present invention relates to material chemistry, molecular biology, and immunology. More particularly, this invention describes the application of porous framework materials in storage, transportation, and delivery of biomolecules, the development of novel composite biological agent, including related preservation kits, portable medicines, and novel drug delivery systems.

BACKGROUND OF THE INVENTION

With the progress of biological technology, biomolecules have played an increasingly important role in the fields of disease diagnosis, treatment and the like. However, some biomolecules, such as vaccines, antibodies, conventional proteins, enzymes and the like are easily affected by external factors and lose their activity. For example, vaccines, antibodies, and protein drugs and the like are very sensitive to temperature and need low-temperature for stable storage and transportation. To ensure low temperature, a professional equipment for storage and transportation is necessary, and many manpower and material resources will be consumed. Meanwhile, the application of these biomolecules is also restricted. Besides, biomolecules are very sensitive to the environment (e.g. mechanical forces, solvents, chemicals, etc.), which may greatly affect their activity. There are large area and various climatic and geographical conditions in our country, At the same time, imbalanced development between regions cannot ensure that all biomolecules can be transported and preserved properly in all aspects. Therefore, efficient protection means is urgently needed to reduce the influence of external environmental changes and protect the activity of biomolecules, which can greatly improve the efficiency and application scope of biomolecules, and reduce storage and transportation costs.

Porous frame materials (such as metal-organic frameworks, MOFs; covalent organic frameworks, COFs; hydrogen-bonded organic frameworks, HOFs, etc.) are a new generation of porous materials that have developed rapidly in recent years. Since the porous frame materials have extremely high surface areas, high porosity and easiness in regulation and control of pore size and the like, they can be widely applied in multiple fields, such as gas adsorption and separation, sensors, and catalysis. The porous frame material has good crystallinity, definite spatial structure, and pore environment, that is favorable for the study and analysis of the interaction and related mechanism between the material and guest molecules (e.g. loading and releasing by the materials). And the application value of the porous framework material in the field of biomedicine begins to attract attention due to the extraordinary properties. At present, the applications of porous frame materials in the biological field are mainly focused on biosensors and immobilized enzymes. The stability of enzymes immobilized or encapsulated by porous frame materials has been improved. Through systematic and deeply research on the interaction mechanism and preparation strategy of protein, vaccine and other biomolecules using porous frame materials, this invention has designed and developed novel technologies that can be applied to the protection of biological agents, which can maintain the activity of biomolecules against harsh environment (such as high temperature, mechanical force, chemical agent pollution, etc.), and can be used for the storage and transportation of biological agents at room temperature. Besides, the invention can simply and quickly realize the controllable and high-efficiency release of biomolecules. According to the invention, an innovative application of porous frame materials in the preservation of biomolecules is researched and developed for the first time, various performances are comprehensively tested and evaluated. This invention also solves technical problems of synthesis, preservation, and release process. The porous framework material has a wide application prospect.

Most biomolecules are protein biomolecules, and their environmental stability is different due to their various structures. However, the degradation and functional deficiency of protein biomolecules can be attributed to the following reasons: 1) The desamidization of asparagine and glutamine residues in proteins, asparagine and glutamine change to aspartic acid and glutamic acid under certain conditions, leading to the loss of protein activity. 2) the secondary and tertiary structure are changed; 3) Many proteins suffer from their own characteristics such as flexible branch chain and peptide bond rupture under mechanical conditions, pH changes, temperature changes, etc. After protected by porous frame materials, protein domains can be bolted effectively to remain stable.

This invention is to provide a novel technology to solve the storage, transportation, and delivery of biomolecules at room temperature. This technology is simple, efficient, and low in cost, which also can significantly improve the stability of biomolecules against temperature changes, mechanical forces, chemical treatment and the like. By improving the stability of biomolecules, the difficulty and cost of their preservation can be effectively reduced. Meanwhile, because the biomolecule-porous material composite has a strong resistance towards mechanical force, it can be processed into various forms as required, such as kits, portable drug delivery systems, which has wide application prospects.

OBJECTS AND SUMMARY OF THE INVENTION

Therefore, it is an object of the claimed invention to provide a significantly improved the present invention is directed to a composite biological agent, which is easy to store, transport, deliver, portable and easy to use. Also, the present invention is directed to a preparation of the composite biological agent, which is creatively obtained by reaction of biomolecules and porous framework materials (e.g., metal-organic framework materials, MOF; A covalent organic framework material, COF; The hydrogen bond organic framework material, HOF and the like). The composite biological agent can efficiently protect biomolecules (including proteins, antibodies, viruses, vaccines, enzymes, and other biomolecules) against harsh environments (such as mechanical force, inhibitor, chemical reagent, etc., and the change of solvent, temperature, pH, humidity, etc.), and also enhance their stability for long term and room temperature storage, transportation and application. At the same time, the systems of the technology can release the encapsulated biomolecules (guest molecules) under specific environment as desired. The present invention solves the key problems in the storage, transportation, and use of biomolecules, which stabilizes the biomolecules, reduces the storage and transportation cost, and facilitates the use of biomolecules. The composite biological agent can release biomolecules as required. Besides, the present invention greatly improves the mechanical processing performance and stability of biomolecules, and also provides a novel solution for further processing the biomolecules.

In a first aspect, the present invention provides a novel biological composite agent based on porous frame materials, which comprises porous frame materials and biomolecules encapsulated by the porous frame materials.

Preferably, the porous frame materials include at least one of metal-organic framework materials (MOFs), covalent organic framework materials (COFs) and hydrogen-bonded organic framework materials (HOFs)

Preferably, the biomolecules include at least one of antibodies, enzymes, peptides, vaccines, nucleotide, and virus species.

Preferably, the encapsulating method included: adsorption, covalence, embedding, and cross-linking; wherein the embedding method included: mix metals, ligands, or monomers with the biomolecules in a ratio of 500-20:1 to form the composite biological agent.

Preferably, the biomolecules can be stored and transported at room temperature for a long period of time in the form of complex prepared by porous frame materials and biological molecules.

Preferably, the composite biological agent can be used after a treatment which is at 50-80° C., pH 2-12, and in organic solvent of methanol, acetone, acetonitrile, tetrahydrofuran, dimethyl sulfoxide, N, N-dimethyl formamide, dichloromethane, n-hexane or anhydrous ether.

Preferably, the composite biological agent can release the biomolecules in the following conditons: 1) the pH value is 4-9, 2) the temperature is 20-30° C., and 3) the solvent is one of physiological buffer solution, water or EDTA.

Preferably, the composite biological agent can be used for preparation of biomolecules preservation kits, portable drugs, and novel drug delivery systems.

Preferably, the porous frame materials are one or more of ZIF-8, ZIF-11, ZIF-90, and MIL-53. If the porous frame materials and biomolecule composite are obtained by adsorption, covalent, embedding, and cross-linking, etc., the porous frame materials can be selected from COFs of PI-1-COF, PI-2-COF, TTI-COF, COF-OMe and COF-OH; MOFs of HKUST-1, MIL-101, MIL-100, MIL-53, PCN-777, Tb-mesoMOF and PCN-222, or HOFs of HOF-5, 1-Val-1-Ala and MPM-1-Br, or a combination of more.

Preferably, the porous frame materials may be metal-organic frameworks (MOFs). MOFs are constructed by metal ions (or metal cluster) and organic ligands with specific functional groups and shapes, so that the MOFs material with proper pore size and shape, high surface area and high porosity and good thermal and solvent stability can be well designed to match specific applications. Such as: ZIF-8, ZIF-90, ZIF-1, ZIF-100, Tb-BDC, Eu-BDC, PCN-333, MIL-88A. HKUST-1, MIL-101, MIL-100, MIL-53, PCN-777, Tb-mesoMOF, PCN-222, etc.

Preferably, the porous frame materials are covalent organic frameworks (COFs). Covalent organic framework material is an organic porous material with ordered structure formed by covalent bonding of organic building units (ligands), which has the characteristics of high specific surface area, high pore rate, regular pore size, easy regulation, flexible structure, easy functionalization, and has excellent thermal and chemical stability. Such as: PM-COF, PI-COF-2, TTI-COF, COF-OMe, COF-OH, etc.

Preferably, the porous frame materials are hydrogen bonded organic frameworks (HOFs). Hydrogen bonded organic frameworks are defined as frameworks connected through H-bonding interactions between the organic units including both pure organic and metal-containing organic moieties. HOFs feature high surface area, low mass density, tunable pore size, high thermal and chemical stability, and easily tailored functionality and flexible structure. Both COFs and HOFs can be designed and synthesized as carrier materials with appropriate pore size and shape, high specific surface area, good thermal and solvent stability according to their needs.

Porous frame materials feature easily tailored functionality, easy to adjust, flexible, and clarify structure. After a long-term experiment, we have optimized the synthesis process of some porous frame materials, such as shortening the reaction time, expanding the reaction temperature range, and simplifying the operation. The strategy provided by the invention has the characteristics of simplicity in operation, mild conditions, good stability, good biomolecules recovery rate, easiness in obtaining of required raw materials and the like.

The invention provides the composite biological agent. Biomolecules that can be protected by this application include but are not limited to proteins, antibodies, viruses, vaccines, enzymes, polypeptides, nucleic acids, etc.

The porous frame materials used for the application of biomolecules preservation are characterized in the reaction system that can form a composite with biomolecules without destroying their activity.

Preferably, the composite biological agent can mildly release biomolecules under specific condition (such as specific pH, solution, temperature, etc.) as desired. The characteristic can also be that the porous frame materials can be simply decomposed without affecting the activity of biomolecules. Biomolecules can be separated by common physical and chemical means such as, ultrafiltration, molecular sieves, protein gel electrophoresis, etc. The characteristic can also be that certain porous frame materials can gently release biomolecules, without disrupting the structure of the porous framework materials.

The porous frame materials selected for this invention can form a composite with the biomolecules to improve the stability of the biomolecules and improve their resistance to various environmental changes, wherein the environmental changes include at least one of mechanical force, inhibitors, chemical agents, solvents, temperature, pH and humidity, etc.

Preferably, the stability of the biomolecules protected (preserved) by the porous frame materials is equivalent to or superior to the traditional biomolecules in storage, wherein the traditional storage method is freeze-drying, cryogenic storage after using a stabilizer, etc.

In a second aspect, the invention provides a strategy for the preservation of biomolecules (such as antibodies, enzymes, vaccines, proteins, etc.). The composite biological agent is composed of biomolecules and porous frame materials, some of which can be released in a specific environment (pH 4-9, room temperature, physiological buffer, or water). It greatly improves the stability of biomolecules, tolerance to the hash environment with good processability. It can become a novel dosage form of biomolecules, which reduce the cost of storage and transportation of biomolecules, and facilitate the wide application of biomolecules.

Preferably, the method in which the porous frame material forms a composite with the biomolecule includes but is not limited to, the "one-pot" reaction, in which the precursor of the framework material and the biomolecule to form the biomolecule porous frame material complex, or the formed porous frame material encapsulates the biomolecule using adsorption, covalent, embedding, crosslinking, etc.

At the same time, we screened a variety of porous frame materials with good biocompatibility and low toxicity. In this application, the strategy of separating the solution and biomolecules after dissolving the materials further reduces the possible biosafety risks of the materials.

Various other objects, advantages and features of the present invention will become readily apparent from the ensuing detailed description, and the novel features will be particularly pointed out in the appended claims.

BRIEF DESCRIPTION OF FIGURES

The following detailed descriptions, given by way of example, and not intended to limit the present invention solely thereto, will be best be understood in conjunction with the accompanying figures.

DETAILED DESCRIPTION OF THE EMBODIMENTS

Figure 1:
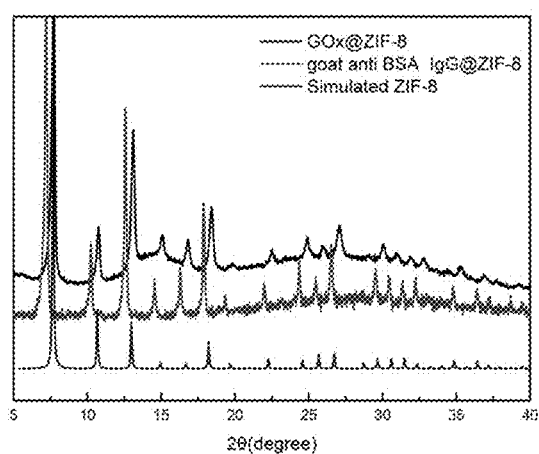
FIG. 1 is an X-ray powder pattern of MOF-1/goat anti-BSA IgG complex and MOF-1/GOx complex (MOF-1 refers specifically to ZIF-8, goat anti-BSA IgG refers to goat Anti-BSA IgG)
Figure 2:
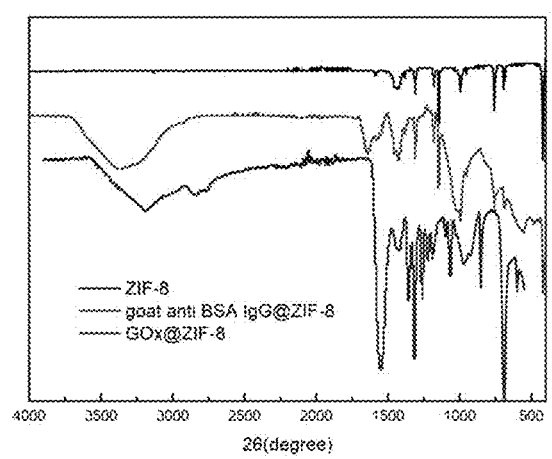
FIG. 2 is a Fourier infrared transform spectrum of MOF-1/goat anti-BSA IgG complex and MOF-1/GOx complex.

Referring to FIG. 1-FIG. 13, the synthesis of the porous frame materials, the characterization test and the method for testing the activity of the active substance, the specific implementation manner is as follows.

The vaccines and antibodies treated by the method in this invention, are dissolved and injected to the rat, and compare with the control group. The experiment results show that the solution system of this method is safe to organism and has no adverse reaction.

If not specifically illustrated, all materials of the invention may be commercially available; or can be prepared according to conventional methods in the art. Unless otherwise defined or specified, all professional and scientific terms used herein have the same meanings as those well-known by the skilled in the art. Furthermore, any methods and materials similar or equal to those described can be used in the methods of the invention.

Features mentioned in the invention and features mentioned in the examples may be combined. All of the features disclosed in this specification may be used simultaneously in any forms of combination; and each feature disclosed in the specification may be substituted by any alternative features providing same, equal or similar purpose. Therefore, unless otherwise specified, the disclosed features are only common examples of equal or similar features.

Referring to FIGS. 1 to 13, the invention is described in detail in connection with the following examples, which are not construed as limiting the scope of the invention.

Raw Materials

All chemical reagents are commercially available products.

Example 1

Preparation of MOF-1/Goat Anti-BSA IgG Complex:

Preparation of MOF-1/goat anti-BSA IgG complex: The PBS solution containing 50 μL and 10 mg/mL Goat anti BSA IgG (Goat anti bovine serum albumin IgG), mixed with 200 μL aqueous solution of 200 mM imidazole compounds, and then 40 mM 250 μL zinc ion aqueous solution was added into the protein-imidazole aqueous solution. μL These two solutions were mixed and placed at room temperature for 10 min. Subsequently, the as-synthesized products were collected by centrifugation (6,000 rmp) for 10 min, washed with excess D.I. water, and then pre-frozen at −80° C., and then lyophilized for 8 hours. (FIG. 1, X-ray powder pattern, FIG. 2, Fourier infrared transform spectrum). The experimental results are shown that the anti-BSA IgG antibody is encapsulated into MOF-1.

Preparation of MOF-1/GOx Complex:

Preparation of MOF-1/GOx complex: Antibody of 0.5 mg was added into a solution of imidazoles (1600 mM, pH 10.3, 250 μL). Zinc ion solution was also prepared in DI water (40 mM, 250 μL). These two solutions were mixed and placed at 4° C. for 12 h. Subsequently, the as-synthesized products were collected by centrifugation (6,000 rmp) for 10 min, washed with excess D.I. water, and then pre-frozen at −80° C., and then lyophilized for 8 hours. (FIG. 1, X-ray powder pattern, FIG. 2, Fourier infrared transform spectrum). The experimental results are shown that the anti-BSA IgG antibody is encapsulated into MOF-1.

Example 2

Figure 3:
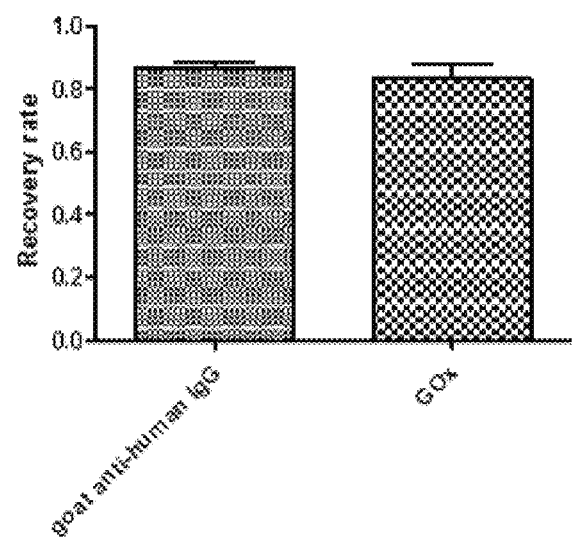
FIG. 3 is a result of recovery rate of encapsulated IgG antibody and GOx enzyme released from MOF-1/goat anti-BSA IgG complex and MOF-1/GOx complex.

Experiment of recovering encapsulated goat anti-BSA IgG antibody and GOx enzyme from MOF-1/goat anti-BSA IgG complex and MOF-1/GOx complex: The recovered and lyophilized MOF-1/goat anti-BSA complex and MOF-1/GOx complex were mixed with the same 20 mM EDTA solution as the reaction system, and after reacting for 15 minutes, the mixture was briefly centrifuged for 5 seconds using a centrifuge. And then ultrafiltration was performed for 10-20 minutes at 10000 g (The specific time depends on the concentration and molecular weight of the protein biologic and the pore size of the ultrafiltration membrane filter used). After the ultrafiltration, the antibody was recovered by washing the ultrafiltration membrane with 1× PBS. The concentration of the recovered antibody was measured using the A280 method to obtain recovery amount data. After calculation, it is compared with the total amount of antibody originally added. The final recovery rate is not less than 80%. Recovery rate=the amount of biologics recovered/the amount of biologics initially added to the system ×100%. The recovery rate experimental results are shown in FIG. 3. As can be seen from FIG. 3, the method developed by this application has a good recovery rate for both IgG antibodies and enzymes.

(FIG. 3, recovery rate of encapsulated IgG antibody and GOx enzyme released from MOF-1/goat anti-BSA IgG complex and MOF-1/GOx complex).

Example 3

Antibody Protection Testing.

Goat anti-BSA IgG solution (0.5 mg/ml) and goat anti-BSA IgG/MOF-1 complex generate were treated under three different conditions. Heating test: high temperature 50-75° C. in 1-5 ml reaction tube, temperature change test: 4-60° C. (20° C./min temperature gradient change) and −8° C. room temperature repeated freezing and thawing experimental conditions to carry out the heat stress test of the protected antibody and protein. Metal oxidation test: the antibody samples and the ascorbic acid and 0.08 mM CuCl2 incubated at room temperature for 3 h. Mechanical test: The mechanical pressure treatment for goat anti-BSA IgG/MOF-1 complex is conducted by a tablet machine with 20 MPa pressure.

Example 4

Size-Exclusion Chromatography HPLC

Size exclusion chromatography HPLC was used to detect the molecular weight of the antibody and the antibody in the complex after several treatments in Example 3. SEC was performed on an HPLC using a pre-prepared column (300 mm×7.8 mm). Each sample (Free IgGs or IgGs recovered from antibody@MOFs) (300 μL) was injected and separation was performed at a flow rate of 0.5 mL/min. The elution buffer was composed of 100 mM sodium phosphate and 100 mM sodium sulfate at pH 7.1. UV detection was performed at 280 nm, while multi-angle laser light scattering (MALLS) detection is performed at 658 nm using an 18-angle detector operating with a 50-nW solid-state laser. The extinction coefficient is 1.69 (mL mg$^{-1}$ cm$^{-1}$), the second dimensional coefficient dn/dc of 0.185 (mL/g) is 0. The AUC of the UV signal was used to calculate the percentage of fragments, monomers, oligomers, protein recovery and total aggregation. For relative protein recovery, the total AUC of the stressed samples with the total AUC of the unstressed samples (it is set to 100%) is compared. The total aggregation percentage considers the oligomer, and the percentage of protein that has not been recovered, which usually contains aggregates that are too large to enter the column. The experimental results are shown in Table 1

|  | fragment | monomer | oligomer |
|---|---|---|---|
| untreated goat anti BSA IgG samples | 1.5 | 97 | 1.5 |
| Heated MOF-1 encapsulated samples | 1.5 | 94.4 | 4 |
| Heated samples | 70.1 | 25.4 | 4 |
| Metal oxidation MOF-1 encapsulated samples | 4.3 | 72.4 | 4 |

-continued

|  | fragment | monomer | oligomer |
|---|---|---|---|
| Metal oxidation samples | 99 | 1 | — |
| Mechanical force treatment MOF-1 encapsulated samples | 1.5 | 95 | 3.5 |

The results illustrated that antibodies@MOFs exhibited good resistance against heated treatment, metal oxidation, mechanical pressure.

Example 5

The Binding Ability Experiment of the Antibody Released from the MOF-1/Goat Anti-BSA IgG Complex:

96-well plates were coated overnight with 100 ng/mL BSA in PBS (100 μL/well). Removed the BSA solution, then the residual binding sites were blocked by incubation step with 5% skim milk solution (200 μL/well) for 2 h at 37° C. Removed the skim milk solution, following by 4 times of washing with 0.05% PBST. Free goat anti-BSA IgG and goat anti-BSA IgG released from MOF-1/goat anti-BSA IgG was diluted at various concentrations (initial concentration was 18 μg/mL, 3-fold dilution) in 1% BSA, and then added 50 μL/well to the plate and incubated for 1 h at 37° C. Samples were then removed and followed with thorough washing. HRP conjugated rabbit anti-goat IgG antibody was diluted to 1:2000 using 1% BSA, and 50 μL/well was added to the plate. Subsequently, incubation was performed for 45 min at 37° C. After removing the solution, all wells were washed with PBST. Next, TMB (100 μL/well) were added to each well and incubated for 15 min in the dark at room temperature. The reaction was stopped by adding 2 N H2SO4 (50 μL/well), and absorbance was measured at 450 nm using microplate reader.

Figure 4:
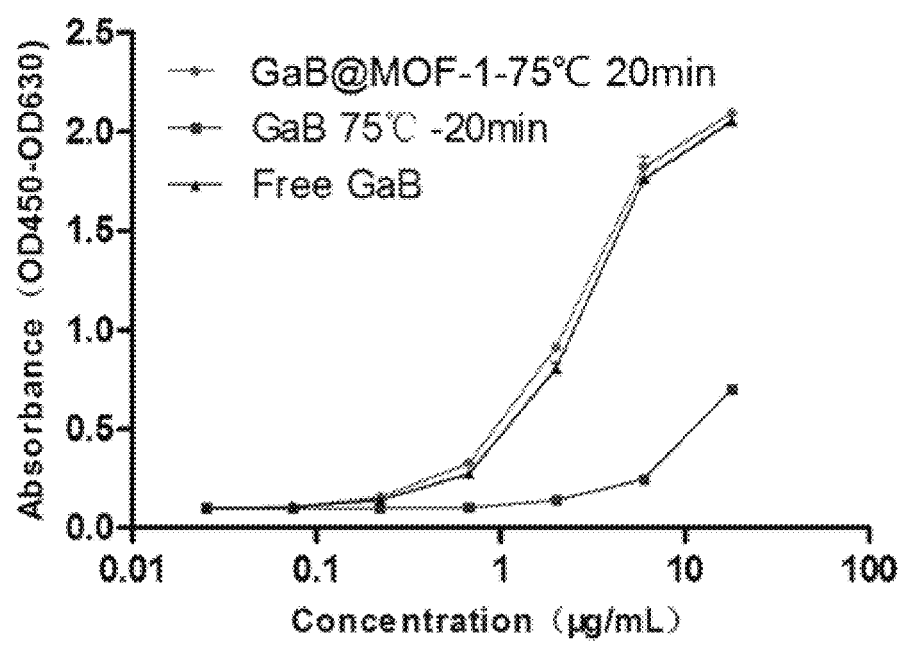
FIGS. 4,5,6 and 7 are the comparison chart of the binding activity of goat anti-BSA IgG released from treated MOF-1/goat anti-BSA IgG complex and treated free goat anti-BSA IgG.

Bingding capacity assay showed that goat anti-BSA IgG released from MOF-1 (after heating at 75° C. for 20 minutes) possessed similar binding abilities as their original antigen of untreated G-IgG (>90%), whereas the unprotected G-IgG almost lost all binding activity, (FIG. 4, binding activity of goat anti-BSA IgG released from treated MOF-1/goat anti-BSA IgG complex and treated free goat anti-BSA IgG after heating at 75° C. for 20 minutes)

Figure 5:
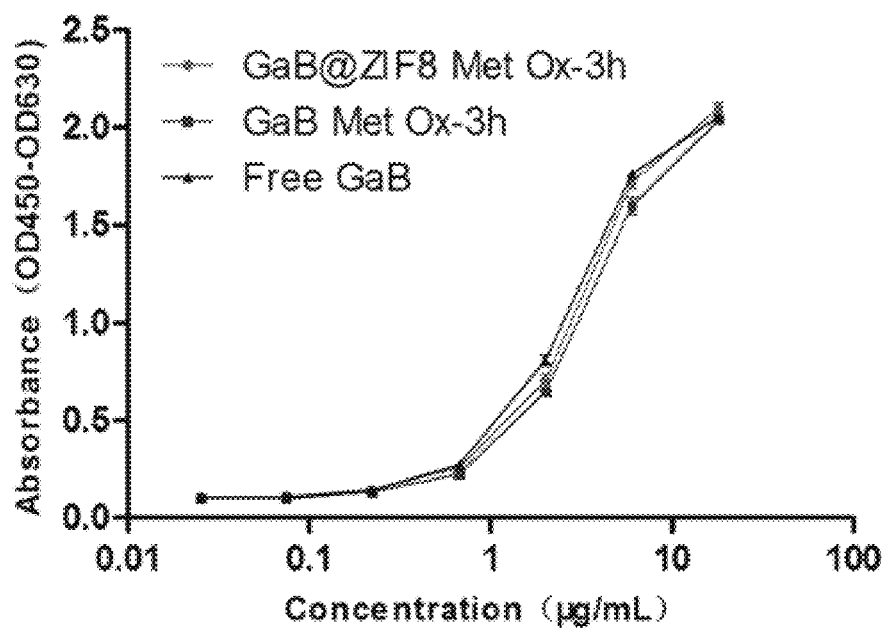

Bingding capacity assay showed that goat anti-BSA IgG released from MOF-1 (after metal oxidation for 3 h) possessed similar binding abilities as their original antigen of untreated G-IgG (>90%), whereas the unprotected G-IgG almost lost all binding activity, (FIG. 5, binding activity of goat anti-BSA IgG released from treated MOF-1/goat anti-BSA IgG complex and treated free goat anti-BSA IgG after metal oxidation for 3 h)

Figure 6:
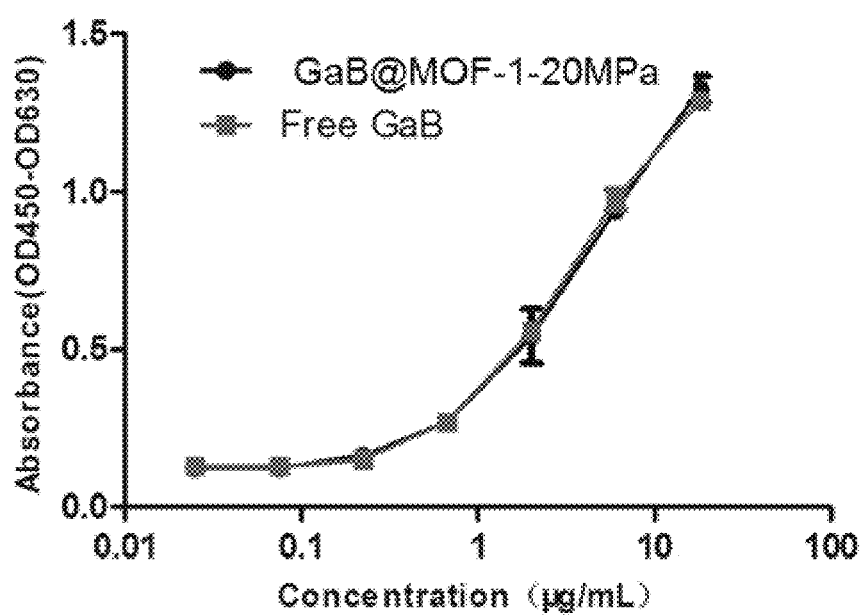

Bingding capacity assay showed that goat anti-BSA IgG released from MOF-1 (after treated at a pressure of 20 MPa) possessed similar binding abilities as their original antigen of untreated G-IgG (>90%), whereas the unprotected G-IgG almost lost all binding activity, (FIG. 6, binding activity of goat anti-BSA IgG released from treated MOF-1/goat anti-BSA IgG complex and treated free goat anti-BSA IgG after treated at a pressure of 20 MPa)

Figure 7:
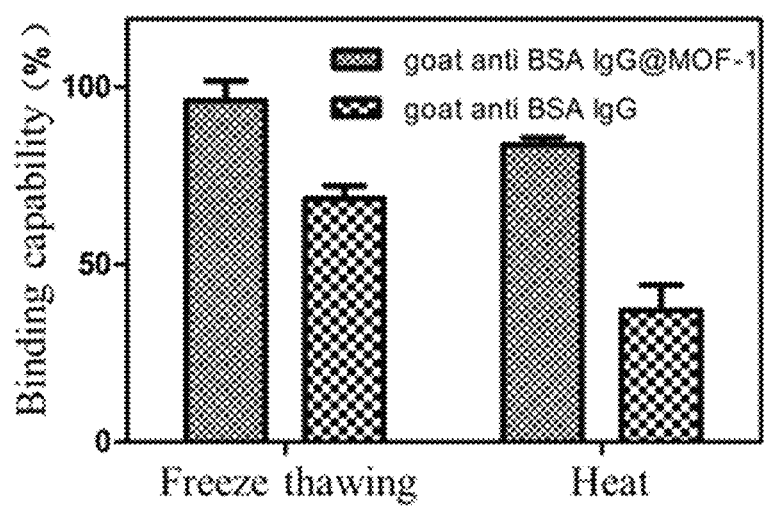

Bingding capacity assay showed that goat anti-BSA IgG released from MOF-1 (after repeated freezing and thawing) possessed similar binding abilities as their original antigen of untreated G-IgG (>90%), whereas the unprotected G-IgG almost lost all binding activity, (FIG. 7, binding activity of goat anti-BSA IgG released from treated MOF-1/goat anti- BSA IgG complex and treated free goat anti-BSA IgG after repeated freezing and thawing)

Example 6

Figure 8:
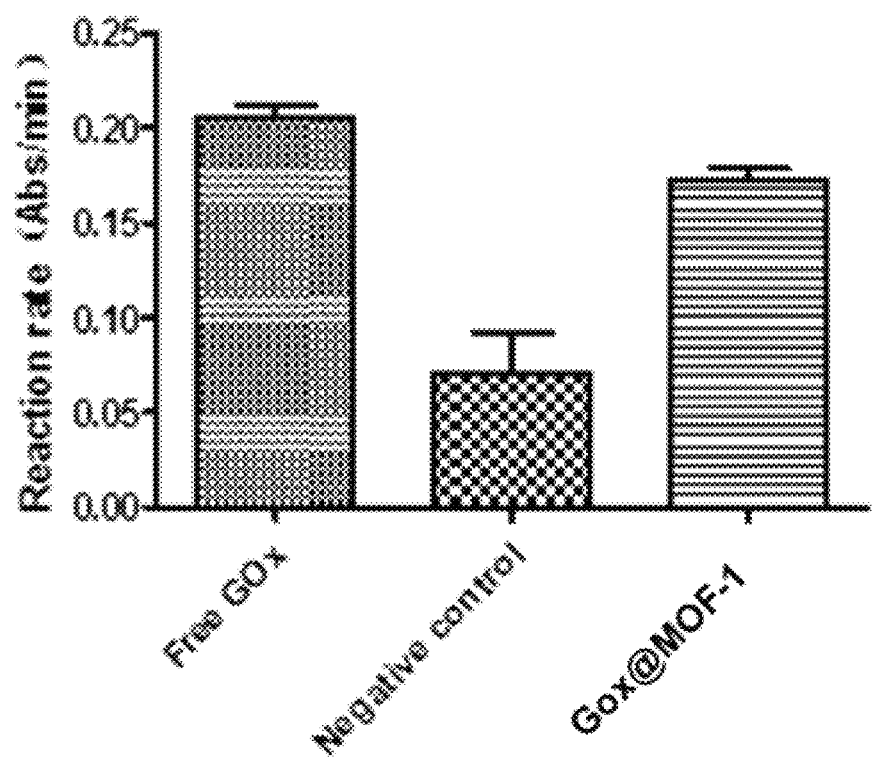
FIG. 8,9 is a comparison chart of initial rate and conversion rate of GOx released from the MOF-1/GOx complex and free GOx.

Comparing the Activity of GOx Released from the MOF-1/GOx Complex with GOx not Encapsulated by MOF-1:

The GOx from the MOF-1/GOx Complex is Released by the Method in Example 2. To quantify GOx and free GOx in the complex, 10 μg of free GOx and GOx from the MOF-1/GOx are added into the reaction solution (100 μL 10% glucose, volume solution, horseradish peroxidase, 30 pL 5 mM resorcinol solution) and PBS added to 3 mL, and then measured the absorption value at 420 nm. Compare the initial rate of the reaction 60 s before the reaction and the total conversion amount after the reaction is stopped. The results are shown in FIGS. 8 that the initial reaction rate of GOx released from porous frame materials is slightly lower than that of unencapsulated GOx. It can be seen that the process of forming a complex with the porous frame material and recovering the complex after decomposition has a slight effect on the initial reaction rate of the enzyme GOx.

Figure 9:
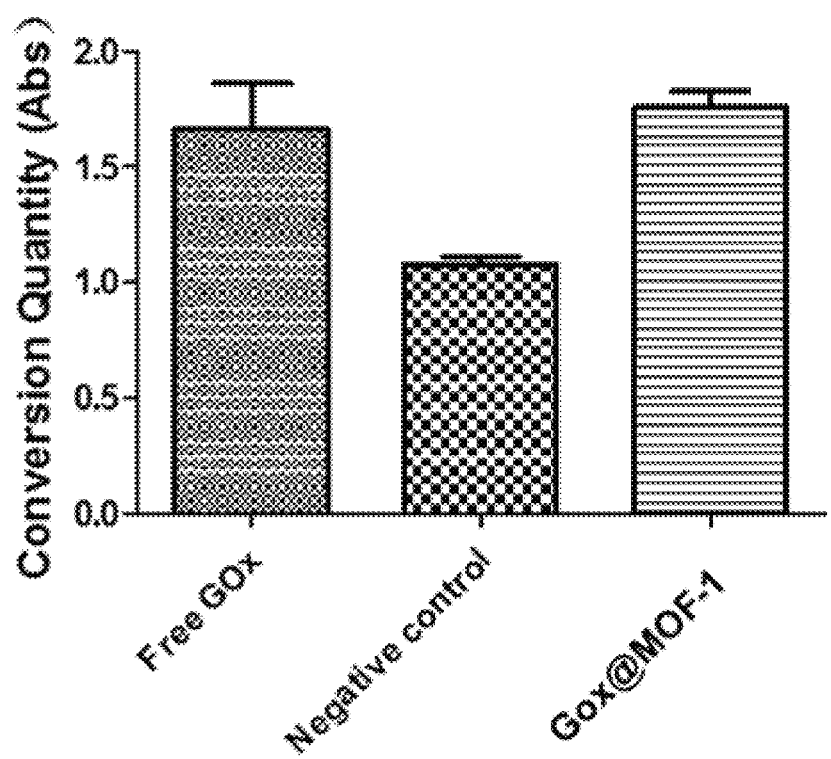
Figure 10:
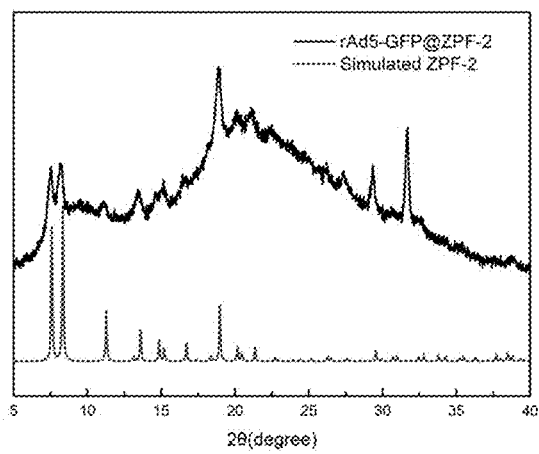
FIG. 10 is an X-ray powder pattern of MOF-2/rAd5-GFP complex (MOF-2 in this application refers specifically to ZPF-2, rAd5-GFP refers to GFP recombinant human adenovirus type 5 viral vector)

The results are shown in FIG. 9 that the conversion rate of GOx released from porous frame materials is slightly lower than that of unencapsulated GOx. It can be seen that the process of forming a complex with the porous frame material and recovering the complex after decomposition has a slight effect on the conversion rate of the enzyme GOx.

Example 7

Preparation of MOF-2/GFP Recombinant Human Adenovirus Type 5 Virus Vector Complex Add desalted rAd5-GFP (GFP recombinant human adenovirus type 5 vector) solution that contains 1 mg virus particles, followed by 2500 μL of the 50-500 mM pyrimidines aqueous solution and 2500 μL of the 50-500 mM zinc ion aqueous solution. Then the reaction mixture will turn turbid immediately. Put the mixture at 4° C. and leave it for 0.5-1 hour. After the reaction, the reaction mixture is centrifuged at 6000 rpm, and the supernatant is discarded to obtain a white solid, which is pre-frozen by −80° C., and then lyophilized for 8 h. (FIG. 10, X-ray powder pattern of MOF-2/rAd5-GFP complex). The experimental results shown that the GFP recombinant human adenovirus type 5 virus vector is encapsulated into MOF-2.

Example 8

Detection of the Protective Effect of Recombinant Adenovirus.

Figure 11:
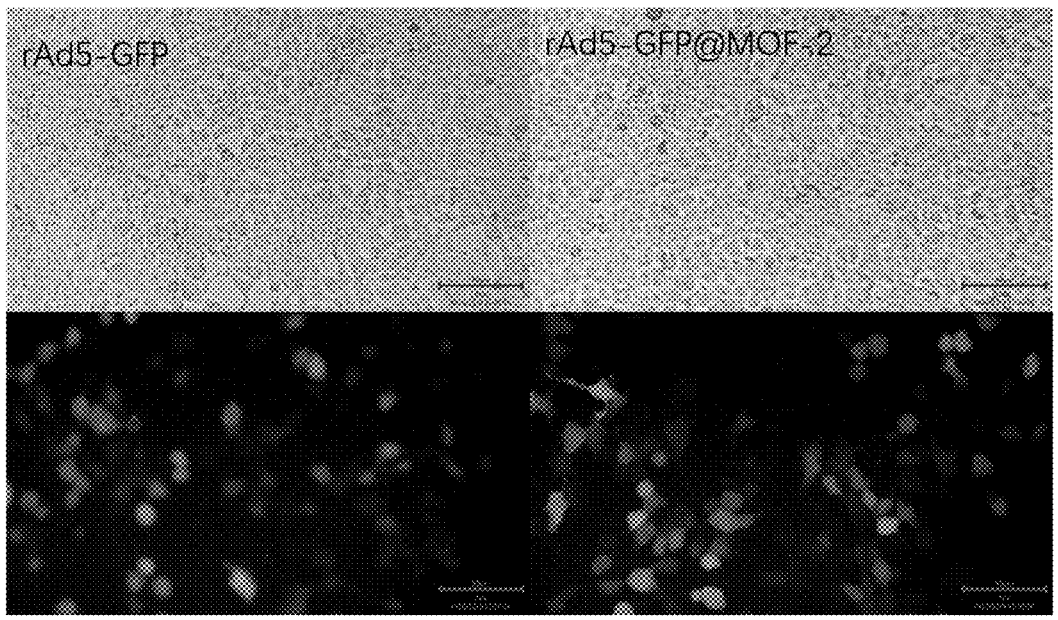
FIG. 11 is a comparison of the cell infectivity of the GFP recombinant human adenovirus type 5 vectors released from the MOF-2/GFP recombinant human adenovirus type 5 virus vector complex.
Figure 12:
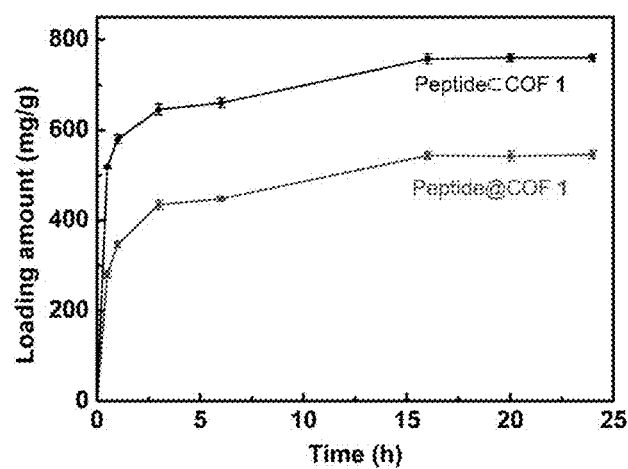
FIG. 12 is a result effect diagram of COF-1/peptide covalent and adsorption.
Figure 13:
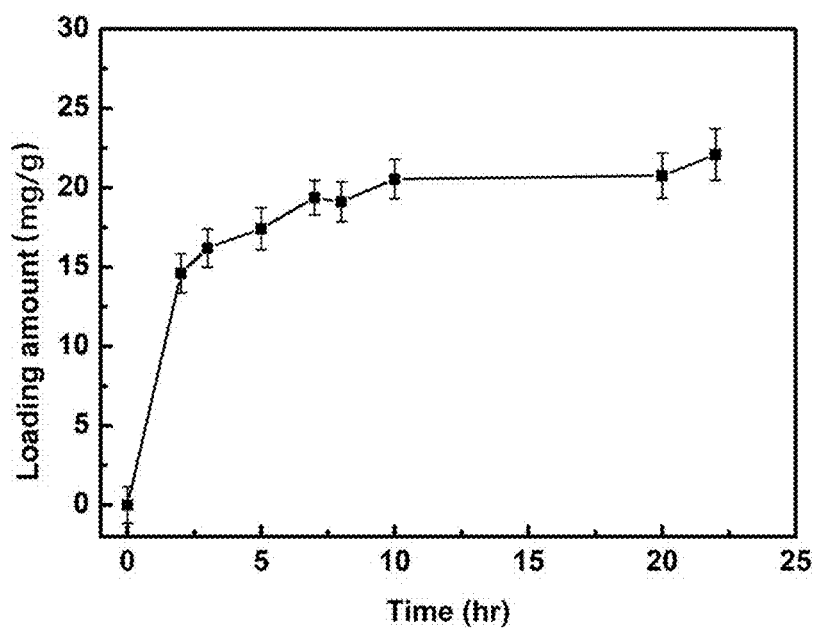
FIG. 13 is an effect diagram of MPM-1-Br adsorption of BSA.

Take 293T cells in the logarithmic growth phase, trypsinize, count, and put into a 24-well plate, 500 μL per well (5×104 cells/mL). Add 50 μL virus samples to each well, then at 37° C., 5% CO2 incubator culture 48 h. Directly observe the number of fluorescent cells in the field of view under a fluorescent microscope. (FIG. 11, comparison of the cell infectivity of the GFP recombinant human adenovirus type 5 vector released from the MOF-2/GFP recombinant human adenovirus type 5 virus vector complex). The experimental results are shown that rAd5-GFP released from MOF-2/rAd5-GFP complex has the same infectivity as free rAd5-GFP.

Example 9

Peptide Covalent and Adsorption Fixation Experiments.

To covalently immobilize biomolecules, the same molar amount of EDC and NHS was first dissolved in 0.1 M MES buffer (pH 6.0), and COF-1 was added into this solution and mixed for 1 h. The NHS-functionalized material was then dispersed in 0.1 M MES buffer (pH 7.0) containing 10.0 mg/mL of peptide. The supernatants were then scanned by UV-Vis (A280 nm, A227.5 nm, and quantified by standard curve for peptide to obtain the amount of peptide covalent immobilized in COF-1. The material COF-1 is directly added to 0.1 MES buffer (pH 7.0) with 10 mg/mL peptide. The supernatants are then scanned by UV-Vis (A227.5 nm, quantified by standard curve for peptide to obtain the amount of peptide adsorption in COF-1. (FIG. 12, effect diagram of COF-1/peptide covalent and adsorption).

Example 10

Adsorption of Vancomycin by Hydrogen Bonding Organic Framework Materials.

Synthesis of hydrogen-bonded organic framework materials: 11 mg of adenine is added into 12 mL methanol, 8.8 mg of copper bromide is added into 12 mL of isopropanol, and then mix them. The isopropyl alcohol solution of copper bromide was added dropwise to cover the methanol solution, and the mixture incubate for one week at room temperature. The product is obtained and washed with methanol to obtain MPM-1-Br. 5 mg MPM-1-Br was add into 2 mL of 5 mg/mL BSA water solution, shaken under 37° C. The supernatants are then scanned by UV-Vis to calculate the amount of BSA adsorbed. (FIG. 13, effect diagram of MPM-1-Br adsorption of BSA). The experimental results are shown that that BSA can be adsorbed into the interior of MPM-1-Br.

Having described at least one of the embodiments of the claimed invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents. Specifically, one or more limitations recited throughout the specification can be combined in any level of details to the extent they are described to improve the present invention. g. 13

What is claimed is:

1. A method for preserving biomolecules, comprising the steps of:
   (1) mixing a metal and a ligand with the biomolecules to form a composite biological agent in which an MOF material is embedded onto the biomolecules;
   (2) leaving the composite biological agent, in which the MOF material encapsulates the biomolecules, at room temperature during storage; and
   (3) processing the composite biological agent with an EDTA solution at 20-30° C. to release the biomolecules from the composite biological agent, wherein:
   the MOF material is ZIF-8;
   the biomolecule is goat anti-BSA or Go$_x$; and
   step (3) includes:
      processing the composite biological agent with the EDTA solution for 15 minutes; and
      centrifugalizing for 5 seconds a processed mixture of the composite biological agent and the EDTA solution.

* * * * *